(12) United States Patent
Hunckler et al.

(10) Patent No.: US 6,652,484 B1
(45) Date of Patent: Nov. 25, 2003

(54) FOOT-POWERED BREASTMILK PUMP WITH REMOVABLE PISTON PUMP

(75) Inventors: Matthew D. Hunckler, South Bend, IN (US); Laura E. Perry, Berkeley, CA (US); Michael L. Perry, Berkeley, CA (US); Brian H. Silver, Cary, IL (US)

(73) Assignee: Medela, Inc., McHenry, IL (US)

(*) Notice: Subject to any disclaimer, the term of this patent is extended or adjusted under 35 U.S.C. 154(b) by 0 days.

(21) Appl. No.: 08/657,356

(22) Filed: Jun. 3, 1996

Related U.S. Application Data (63) Continuation of application No. 08/544,776, filed on Oct. 18, 1995, now abandoned, which is a continuation of application No. 08/434,040, filed on May 2, 1995, now abandoned.

(60) Provisional application No. 60/000,784, filed on Jul. 5, 1995.

(51) Int. Cl.$^7$ ................................................. A61M 1/06
(52) U.S. Cl. .......................................... 604/74; 604/152
(58) Field of Search ............................ 604/73, 74, 151, 604/152; 417/464, 903

(56) References Cited

U.S. PATENT DOCUMENTS

| | | |
|---|---|---|
| 11,135 A | 6/1854 | Needham |
| 128,587 A | 7/1872 | Burgess |
| 684,078 A | 10/1901 | Martin |
| 1,056,865 A | 3/1913 | Webster |
| 1,156,202 A | 10/1915 | Barrett |
| 1,509,226 A | 9/1924 | Brown |
| 1,644,257 A | 10/1927 | Lasker |
| 1,670,610 A | 5/1928 | Colby |
| 2,222,811 A | 11/1940 | Dinesen |
| 2,292,527 A | 8/1942 | Kraft |
| 2,419,795 A | 4/1947 | Saunders |
| 3,782,385 A | 1/1974 | Loyd |

(List continued on next page.)

FOREIGN PATENT DOCUMENTS

| | | |
|---|---|---|
| CH | 251810 | 11/1947 |
| CH | 270694 | 9/1950 |
| CH | 6706/80 | 9/1980 |
| CH | 2782/83 | 5/1983 |
| DE | 395101 | 5/1924 |
| DE | 529424 | 5/1927 |
| DE | 17726 | 7/1953 |
| DE | 1067982 | 10/1959 |
| DE | 8714995 | 2/1988 |
| EP | 0 123 269 | 10/1984 |
| EP | 0 162 358 | 11/1985 |
| FR | 1488446 | 6/1967 |
| GB | 185521 | 9/1922 |
| GB | 271857 | 10/1927 |
| GB | 533493 | 2/1941 |
| GB | 660283 | 11/1951 |
| GB | 762701 | 12/1956 |
| IT | 407293 | 9/1944 |
| SE | 158976 | 3/1957 |

OTHER PUBLICATIONS

Ruth A. Lawrence, M.D.; Breastfeeding A Guide for the Medical Profession; Second Edition; Scientific Library; Apr. 16, 1986.

*Primary Examiner*—Brian L. Casler
*Assistant Examiner*—Cris L. Rodriguez
(74) *Attorney, Agent, or Firm*—Baniak Pine & Gannon (57) ABSTRACT

An improved breast pump assembly has a foot drive to which an otherwise manually operated vacuum pump of a breast pump can be readily and releasably attached to operate the vacuum pump by the foot of the user.

12 Claims, 6 Drawing Sheets

U.S. PATENT DOCUMENTS

| | | |
|---|---|---|
| 3,977,405 A | 8/1976 | Yanase |
| 4,067,332 A | 1/1978 | O'Leary |
| 4,187,845 A | 2/1980 | Dror |
| 4,242,060 A | 12/1980 | Price |
| 4,263,912 A | 4/1981 | Adams |
| 4,289,458 A | 9/1981 | Price |
| 4,311,141 A | 1/1982 | Diamond |
| 4,323,067 A | 4/1982 | Adams |
| 4,573,969 A | 3/1986 | Schlensog et al. |
| 4,583,970 A | 4/1986 | Kirchner |
| 4,673,388 A | 6/1987 | Schlensog et al. |
| 4,680,028 A | 7/1987 | Stuart |
| 4,740,196 A | 4/1988 | Powell |
| 4,759,747 A | 7/1988 | Aida et al. |
| 4,813,932 A | 3/1989 | Hobbs |
| 4,857,051 A | 8/1989 | Larsson |
| 4,892,517 A | 1/1990 | Yuan et al. |
| 4,929,229 A | 5/1990 | Larsson |
| 4,964,851 A | 10/1990 | Larsson |
| 5,007,899 A | 4/1991 | Larsson |
| 5,071,403 A | 12/1991 | Larsson |
| 5,304,129 A | 4/1994 | Forgach |
| 5,358,476 A * | 10/1994 | Wilson ................ 604/74 |
| 5,494,410 A * | 2/1996 | Maier-Laxhuber et al. ... 417/53 |
| 5,601,531 A * | 2/1997 | Silver ................ 604/74 |

\* cited by examiner

FOOT-POWERED BREASTMILK PUMP WITH REMOVABLE PISTON PUMP

This application claims benefit of Provisional Application No. 60/000,784 filed Jul. 5, 1995 and is a continuation of Ser. Nos. 08/554,776 and 08/434,040 filed Oct. 18, 1995 and May 2, 1995 respectively, both abandoned.

FIELD OF THE INVENTION

This invention relates generally to breastmilk pumps, and particularly to breast pumps for use in the expression of mother's milk which include a pump mechanism which can be manually driven, such as a piston pump.

BACKGROUND OF THE INVENTION

Pumps used to extract or express mother's milk are well known. Breastmilk pumps are adapted to massage the breast to relieve it of its contents of milk, such as for storage in a container for later use by an infant.

Breast pumps typically come in two basic types: those that are driven off of a motor, such as an electric motor-driven vacuum source connected to the milk extraction device, as by tubing, and those that are driven by hand, that is, manual pumps. See Medela, Inc. U.S. Pat. Nos. 4,857,051, 4,929,229, 4,964,851, 5,007,899 and 5,071,403, for example, as to the state of the art. These breast pumps ordinarily include a funnelshaped rigid hood, or shield, which is placed over the nipple and a substantial portion of the breast for milk extraction. Actuating the vacuum pump intermittently generates a reduced pressure or vacuum within the shield to create a suction which draws the nipple and adjacent breast further into the narrower portion of the shield. This pulling action both massages and constricts the breast in a manner reminiscent of suckling, resulting in the expression of milk into the funnel opening of the shield. The milk then typically flows into a collecting chamber or container for storage for later use or disposal.

The means generally used for generating the intermittent suction within the shield in a manually driven pump may be a compressible bulb or preferably a pneumatic piston pump. The latter commonly would include a piston cylinder that is connected to the shield, with a piston mounted for reciprocating movement within the piston cylinder, such as under the driving action of a hand-driven piston rod connected at one end to the piston, with the other end extending out of the rear of the piston cylinder. Further details regarding a breast pump with such a manually driven piston pump can be gleaned from the aforementioned U.S. Pat. Nos. 4,875,051 and 5,007,899, for example.

The manually driven breast pump described above has many advantages, such as its relatively compact nature and its operability without an electric power source, enabling it to be readily transported and used anywhere. There are times, however, where transportation of the breast pump and power requirements are not significant factors, such as in the home or in a hospital environment. In those instances, it can be desirable to use some other means to drive the breast pump. Dispensing with the need to manually operate the breast pump frees one of the user's hands; this would allow the pumping of both breasts simultaneously using two breast pump assemblies, considerably speeding up the extraction process.

Disclosed in U.S. Pat. No. 5,007,899 to Larsson, and sold by Medela, Inc. under the name LACTINA, is a motorized drive which can accept the Medela, Inc. manually driven piston pump without modification of the piston pump. The LACTINA motorized drive operates the otherwise manual piston pump, freeing the hands of the mother. Another advantage attendant to the LACTINA motor drive for the manual pump is the ability to isolate the milk extraction equipment, and specifically the piston pump, from the inner workings of the motor drive. The relatively inexpensive manual pump components can thereby become essentially disposable, or at least provided so that each mother of a plurality of women using a single motor drive, as in a hospital environment, will have her own piston pump. Hygienic use of the motor drive is thus enhanced, and the risk of cross-contamination is virtually eliminated.

The ability to readily switch a piston pump between a manual mode and a motor driven mode in the foregoing manner is obviously quite advantageous. A motorized breast pump, however, still requires an electrical supply such as batteries or a wall outlet. The motorized breast pump of necessity can also be somewhat heavy and large, to accommodate the electric motor and drive train.

A manual breast pump that can be actuated by foot instead of by hand offers a general solution to the problems explained above while simultaneously retaining the inherent advantages of the two types of pumps. Currently, there are no foot actuated breast pumps on the market. U.S. Pat. No. 5,304,129 issued Apr. 19, 1994, to Suzanne Forgach describes a breast pump that utilizes a treadle and platform combination to provide a means for operation by foot. However, there are many problems with this design. Such an apparatus is bulky and cumbersome. It requires an awkward motion that does not utilize the larger muscle groups in the legs. It does not provide a sucking action that closely resembles the infant's, which has been shown to provide the most effective means of milk expression. There is no way of cleaning this pump which invariably becomes contaminated over time because of the vapors from the warm milk. Additionally, this prior art does not isolate the milk reservoir from the pump, and therefore it requires a relatively large displacement pump or bellows which further increases the bulk of this device.

SUMMARY OF THE INVENTION

The present invention has as a principal objective to provide a foot drive which can readily and removably accept an otherwise manually operated breast pump, so that the manual pumping elements will be mechanically driven by the foot of the user to generate an alternating negative pressure for milk extraction. Accordingly, the present invention provides an improved breast pump assembly which includes such an otherwise manually operable breast pump in a first mode of operation, which in a second mode of operation is attachable to a foot pedal device adapted to readily receive and then mechanically drive the otherwise hand-drivable pump to effect the expression of mother's milk.

In a third mode of operation, the otherwise manually operable pump can be attached to a LACTINA motor drive to drive the piston pump. The foot powered breast pump of the invention has the advantage of freeing at least one of the user's hands to allow the pumping of both breasts simultaneously or performing other tasks during the pumping process, without the need for a source of electricity to drive a motor. The foot powered breast pump of the present invention is easy to use, and durably constructed. Mechanically operating the breast pump with the larger muscles of the leg reduces fatigue and is also more relaxing for the user.

Another objective of the present invention is to provide for a novel foot actuated breast pump with a lightweight structure which is also simple and inexpensive to manufacture. A particularly noteworthy advantage of the present invention is the capability of the device to store in a compact and protective manner when not in use.

Still another object of the present invention is to provide a simple means for adjusting the maximum amount of suction or negative pressure generated with each pump stroke.

Yet another object of the present invention is to provide a simple means of disassembly of the device for cleaning and/or for conversion to a very portable hand operated breast pump.

To these additional ends, another embodiment has a flexible tubular line that is disconnected and the housing is held in a compact closed position by a locking latch or bail at the end opposite the hinge. The tubular line may optionally be stored within the closed housing.

For transportation and storage purposes it is desirable that the suction device be as compact as possible. Therefore, in the preferred embodiment there are one-way valves located between the funnel shaped receiving members and the collection chambers. The purpose of these valves is to isolate the collection chambers from the receiving members when a vacuum or negative pressure is applied. This enables the, full force of the reciprocating pump to be applied to the receiving members, which allows the volume of the pump to be substantially smaller than would be the case if the collection chambers were not isolated. It will be noted that these valves also offer other advantages such as minimizing the amount of milk vapor that can enter the tubular lines and allowing the collection chambers to consist of plastic bags or liners, since these volumes are no longer affected by the periodic negative pressure. There is furthermore disclosed a means for providing adjustment of the vacuum produced by the device.

DETAILED DESCRIPTION OF PRESENTLY PREFERRED EMBODIMENTS

The improved breast pump assembly illustrated herein includes two principal components. One is a manually operable breast pump, which is shown set up for such manual operation in FIG. 2. The breast pump has a breast-hood or breast-shield assembly 10 and a handdrivable piston pump 11 which connects to the breast-hood assembly in a manner which will be described in more detail hereafter. A container for the collection of breast milk, such as a bottle 12, is attached to the lower portion of the breast-hood assembly 10, as by a screw-threaded attachment.

The manually operable breast pump shown herein, and generally comprised of hood-assembly 10 and piston pump 11 and bottle 12, is substantially the same as that shown in the aforementioned U.S. Pat. No. 4,857,051. Briefly, and with reference to FIGS. 3 and 4, that breast pump has a hood or shield body having two ends. The first or forward end 23a has a substantially wide-section (diameter), and is funnel-shaped. A second or rearward end 23b of the shield constitutes a generally cylindrical extension of the funnel. The second end 23b communicates with a collecting or catch chamber 24 defined by a tubular extension, and with a vacuum passage 25.

Figure 4:
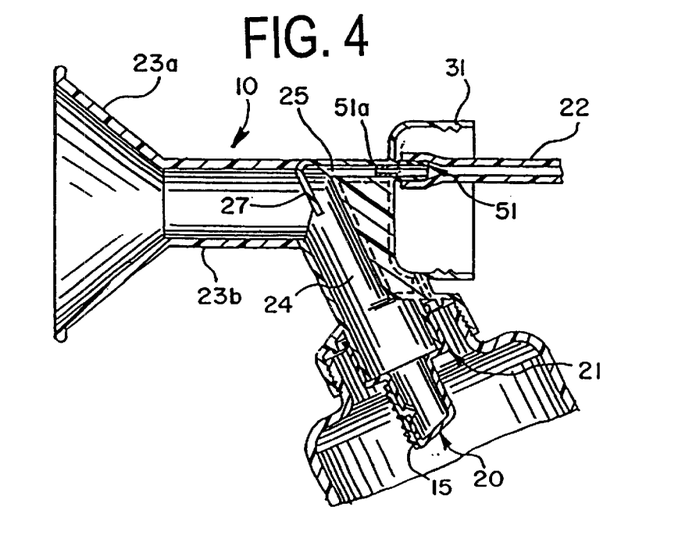
FIG. 4 is an enlarged sectional view detailing the breast-hood assembly.

A downwardly depending separation wall 27 forms a baffle between the second end 23b and the vacuum passage 25, with the bottom of the separation wall 27 below the level of the vacuum passage 25. Milk expressed into the hood member is thus blocked by the separation wall 27 from thereby entering the vacuum passage 25.

At the lower portion of the collecting chamber 24 is a valve mechanism 20. The valve mechanism 20 is described in U.S. Pat. No. 4,929,229, with a flexible disk 15 mounted to cover openings in a valve housing 21 in a flap-valve fashion. When the breast pump is operated, the disk 15 is caused to close apertures in the valve housing 21 under negative pressure, thus closing the collecting chamber 24. When the vacuum is released, milk collected in the collecting chamber 24 flows downwardly into the container 12. The valve housing 21 is attached to the outside of a tubular extension of the collecting chamber 24 via a snug interference fit.

Figure 2:
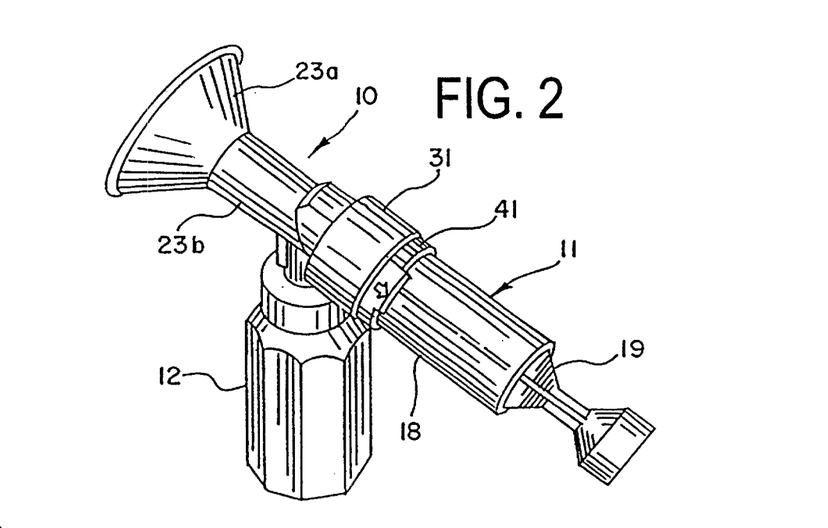
FIG. 2 shows the breast pump of FIG. 1 configured for manual operation.

The manually driven piston pump 11 is formed with a piston rod 19 which is received within a piston cylinder 18 (see, e.g., FIG. 2). Piston pump 11 is connected to the breast-shield assembly 10 by connecting sleeve 31. Connecting sleeve 31, as shown in FIG. 2, is internally screw-threaded, with the threads matched to the screw threads 32 formed on the forward end of the piston cylinder 18 (see FIG. 3). An aperture 35 is formed in the wall of the piston cylinder 18 at a point which corresponds to what is presently considered to be the maximum desired vacuum pressure to be reached on an average stroke of the piston pump 11. Once the head of the piston 21 passes beyond this aperture 35 in its vacuum-inducing stroke, the vacuum produced is automatically released by communication of the aperture 35 with an air passage thereby opened into the cylinder interior.

Figure 3:
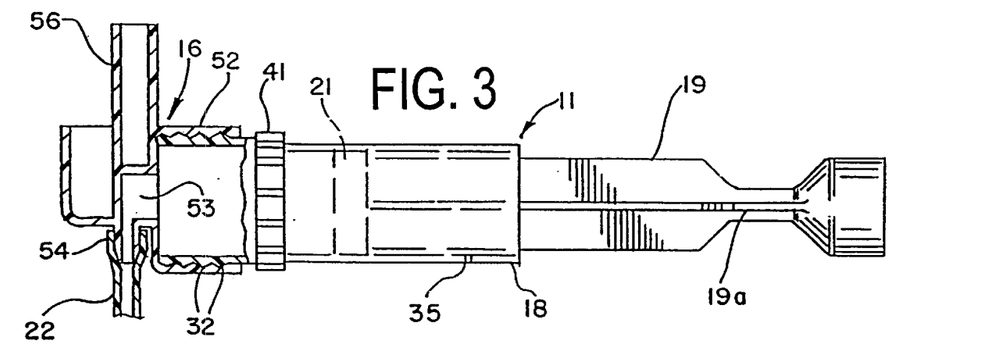
FIG. 3 is an enlarged view partly in section detailing the attachment of the piston pump to an adapter for conversion to operation on another drive.

An adjustment mechanism for varying the amount of vacuum generated during pumping is also provided. This is represented in the illustrations by a ring 41 carried on the piston cylinder 18 adjacent its forward end which overlies a pair of holes (not shown) through the cylinder 18. An interior chamber or channel (also not shown) is formed on the inside of the ring 41. The channel formed in the ring 41 has one or more openings to atmosphere. The ring is rotated to expose one, both or none of the underlying cylinder holes to atmosphere, to thereby adjust the vacuum level generated by the piston pump 11. The ring 41 is preferably made out of a flexible or semiflexible rubber-like material that enables a good seal to be maintained between the ring 41 and the piston cylinder 18. Further detail of this vacuum modulator device are set forth in U.S. Pat. No. 4,857,051.

Referring to FIG. 3, the present breast pump assembly uses an adaptor 16 as again shown in U.S. Pat. No. 5,007,899, the details of which are herein incorporated by reference. Cap portion 52 of the adaptor threads onto piston cylinder 18, sealing the top of piston cylinder 18 to the adapter 16 for a substantially airtight attachment. When it is desired to mechanically drive the piston pump 11, the adaptor 16 is used. In point, and as shown in the aforementioned U.S. Pat. No. 5,007,899, the adapter 16 is used to attach the piston pump 11 to a motor drive (Medela's LACTINA).

FIG. 4 shows the breast-shield 10 with the piston pump 11 removed, and the breast-shield attached to a vacuum source—such as a remotely-driven piston pump 11 —via a length of tube tubular connector 51 has one end 51a is received in the vacuum passage 25, with its other end fitting within the vacuum tube 22. This is shown and described in U.S. Pat. No. 5,007,899.

As seen in FIG. 3, post 56 of the adaptor 16 is received within a post-hole formed on the motor drive housing to anchor the piston pump/adapter. Inside of the cap 52 is a small chamber 53 which communicates with the interior of the cap 52, and therefore also with the piston chamber interior. Extending off the chamber 53 is a nipple-like outlet 54. Outlet 54 is sized to be received within the other end of the tubing 22.

Figures 5, 6, 7:
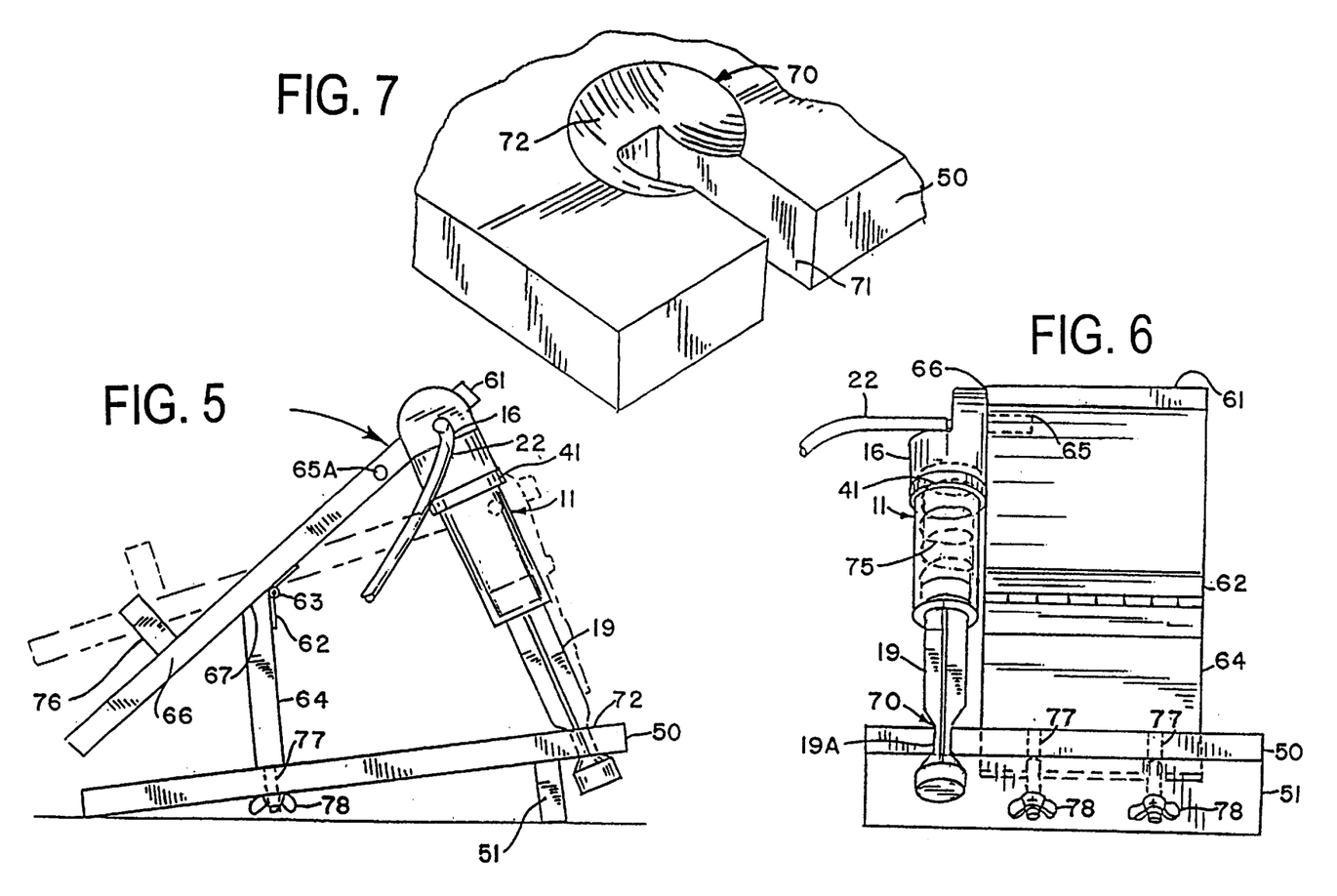
FIGS. 5 and 6 are side and front elevation views, respectively, of the foot drive with the piston pump of FIG. 3 affixed thereto.
FIG. 7 is a perspective view of the base of the foot drive where the piston rod of the piston pump is received.

Referring to FIGS. 5 and 6, the piston pump and adapter arrangement of FIG. 3 has now been adapted to be driven by a foot powered mechanism. The pedal drive has a base 50 which is angled slightly upward toward the user by a leg 51. A foot pedal 61 is pivotably connected to the base 50 via a hinge 62 on a riser 64. Although riser 64 is rigidly attached to base 50, a releasable attachment is used herein. The bottom of riser 64 has two downwardly extending members 77 which extend through a pair of holes in the base 50. The downwardly extending members 77 are threaded to accept a wing nut 78 to attach the riser 64 to the base 50. Hinge 62 is at a hinge point 63 along the length of the foot pedal 61 and toward the middle of the pedal 61. The releasable connection to the base 50 enables the foot drive components to be collapsed to a more compact form for transport or storage.

As best seen in FIG. 7, the base 50 has a cutout 70 at one end to receive the manual pump 11. The piston rod 19 of the pump 11 has a reduced diameter portion 19a received within the cutout 70. The cutout 70 is formed of a slot 71 which extends into a recessed bowl-shaped receptacle 72. The receptacle 72 at the end of the slot 71 has a curvature roughly matching the taper of lower portion of the piston rod 19 in the transition area between portion 19a and the piston rod main body. This contoured receptacle holds the lower end of the pump 11 in place during operation. To remove the pump 11, the piston rod 19 is raised and then slid out of its seat in the receptacle 72.

The foot pedal 61 has a blind post hole 65 bored into its side edge 66 to receive the post 56 of the adapter 16, as seen in FIGS. 5 and 6. A second post hole 65a is additionally provided for a different angulation of the pump, which can accommodate a different stroke length for the piston pump 11.

Preferably, a helical spring 75 (FIG. 6) is also provided within the cylinder chamber. The spring 75 butts against the interior end wall of the adapter 16 and the front end of the piston 21, and serves to bias the piston 21 away from the adapter. During use of the pedal drive, this spring bias places the pedal 61 in a rest position as shown in solid line in FIG. 5, and serves to return the pedal 61 from its depressed position (dotted line in FIG. 5). A spring to bias the pedal 61 in the foregoing manner may alternatively be provided external to the piston cylinder 18, such as directly between the pedal 61 and base 50, or the riser 64.

A heel support 76 is further provided across the lower end of the pedal 61, which is useful in positioning the heel. The heel support 76 is rigidly attached to pedal 61, but may also be releasably attached in a manner similar to riser 64. A toe-strap 88 (FIG. 1) can additionally be provided for foot positioning. The heel support 76 and toe-strap 88 also respectively facilitate use of the foot in driving the piston pump 11 in the vacuum stroke.

Figure 1:
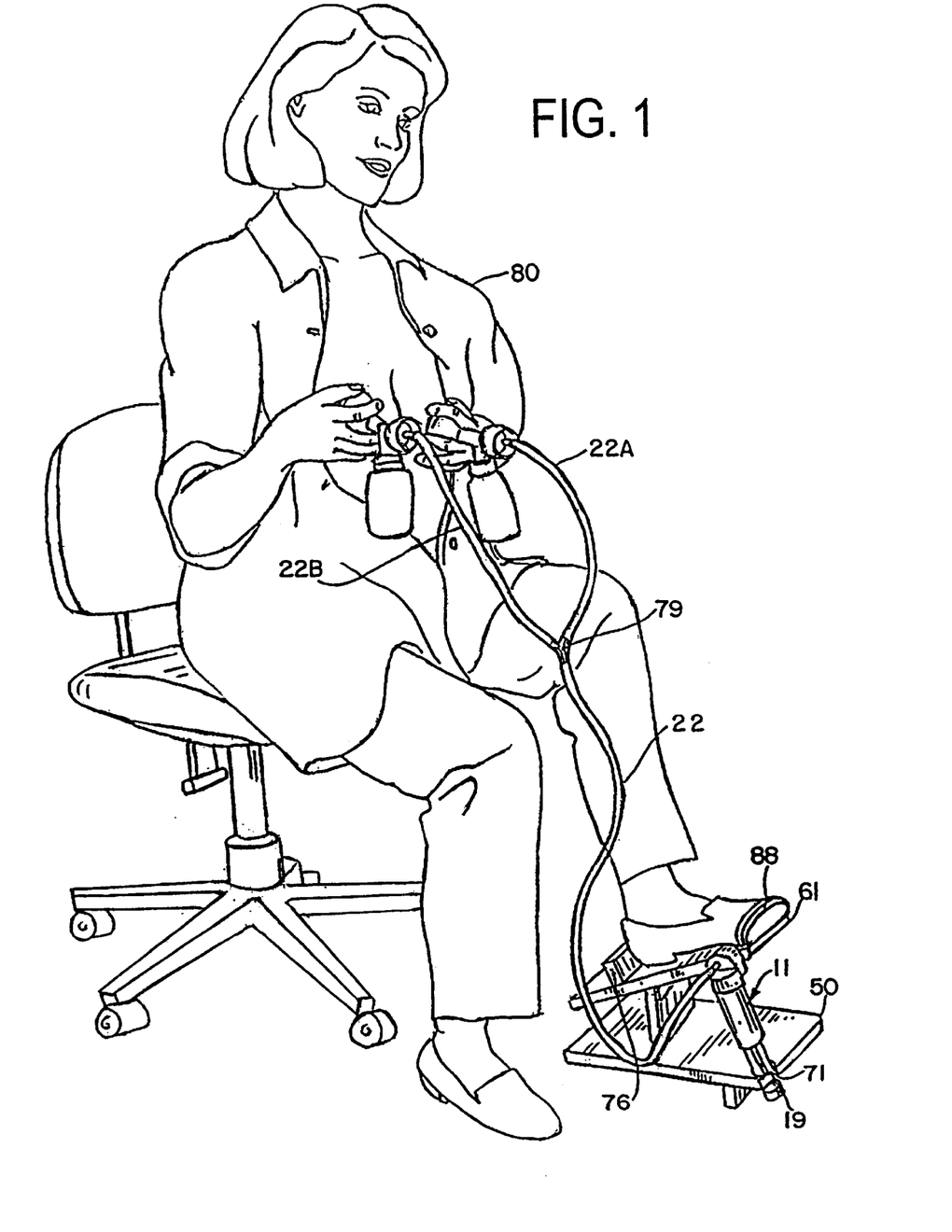
FIG. 1 is a perspective view showing the operation of an improved breast pump assembly in accordance with the present invention.

Fully assembled for use, the pump 11 connected to adaptor 16 is held in place with the piston rod 19 seated into the receptacle 72 of the base 50 and the post 56 of the adapter 16 inserted into a post hole 65, 65a of the foot pedal 61. The pump 11 is thereby held between a "jaw" formed by the base 50 and foot pedal 61. As seen in FIG. 1, the user 80 pivots the foot pedal 61 to operate the pump 11. The user 80 first presses the forward end of the pedal 61 downwardly to thereby force the piston rod 19 into the piston cylinder chamber to decrease the volume therein, and then pivots the forward end of the pedal 61 upwardly to thereby withdraw the piston rod and generate a vacuum (negative pressure) within the cylinder 18, with the vacuum then being communicated to the breast shield assembly (or assemblies) of FIG. 4. As shown in FIG. 5, the riser 64 has a sloped top 67 adapted to allow the pedal 61 to freely pivot until the piston pump 11 reaches the end of its stroke. This pedal drive frees at least one hand, which can allow the mother to pump both breasts simultaneously, such as shown in FIG. 1 (the tubing 22 is connected to separate tubes 22a, 22b to each breast shield assembly via a tubular Y connector 79, as shown in U.S. Pat. No. 4,857,051, for example). The readily releasable piston pump 11 retains all of the advantages attendant to its use on the aforementioned motor drive LACTINA.

Of course, it should be understood that a wide range of changes and modifications can be made to the method and apparatus described above. It is therefore intended that the foregoing detailed description be regarded as illustrative rather than limiting, and that it is the following claims, including all equivalents, which are intended to define the scope of this invention.

Figure 8:
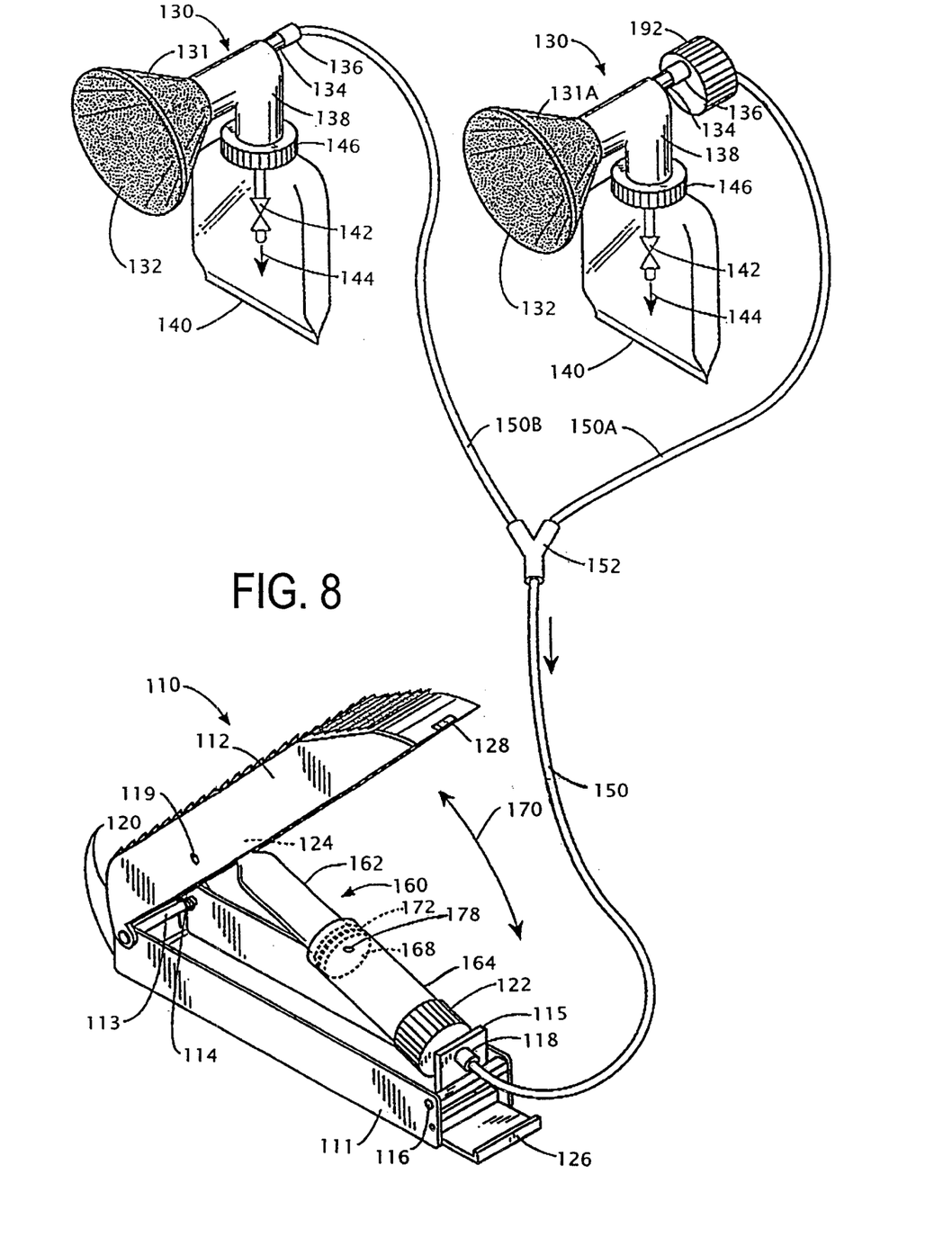
FIG. 8 is an overall perspective view of an assembled foot actuated breast pump, including a foot actuated vacuum pump in the open and operating position along with devices for collecting the expressed milk from both breasts.

Turning now to FIG. 8, another embodiment of a breast pump made in accordance with the teachings of the present invention is shown. This arrangement consists of a foot actuated suction device or vacuum pump 110 that is attached to two collection assemblies 130, which consist of funnel-shaped receiving members 131 attached to their respective collection chambers 140. Foot pump 110 is connected to collection assemblies 130 by a flexible tubular line 150 that consists of a "Y" or three-way connector 152 with separate tubular lines 150A and 150B attached.

The collection assemblies 130 are well known and have been extensively described in the prior art. Briefly, receiving member 131 consists of a funnel shaped receptacle 132 which is designed to fit over the women's nipple and form an air-tight seal when pressed against the breast. This member may also utilize inserts or liners (not shown) to enhance the fit on breasts of various sizes and shapes. On the narrow end of receiving member 131 there are two openings. An upper opening 134 provides for the passage of air between receiving member 131 and foot pump 110. There is a male or female fitting 136 at one end that provides a means for tubular line 150 to be attached in an air-tight manner. A lower opening 138 is of a sufficient size to permit the flow of expressed milk into the attached collection chamber 140. In the preferred embodiment of the present invention there is also a one-way valve 142 located below lower opening 138 between receiving member 131 and collection chamber 140. Valve 142 is thus preferably located inside collection chamber 140 for simple access and is removable for easy cleaning. Valve 142 may consist of any conventional construction, for example—a ball or flap mechanism, which allows flow in only one direction. In this case, flow is restricted to the downward direction 144. When a negative pressure is applied to receiving member 131 by foot pump 110, via tubular line 150 and upper opening 134, the collection chamber 140 is thereby isolated and unaffected. Collection chambers 140 can be of any size and shape sufficient to accommodate valve 142 and at least four ounces of fluid. Collection chambers 140 may consist of collapsible plastic containers or, alternatively, they may be rigid containers that may also be used to hold plastic bags or liners (not shown) that are commonly sold as "disposable bottles" to store breast milk for later use. It will be appreciated that collapsible containers or these liners may be filled directly with the present invention because of the oneway valve 142. The opening or mouth of collection chamber 140 is fitted with male threads (not shown) which fit into receiving member 131 such that the receiving member serves as a top or cap 146 for collection chamber 140. This arrangement allows for simple access to the milk product and for easy cleaning. Preferably, the mouth of the collection chamber is sized and threaded so that it may also accommodate standard nursing bottle caps with nipples.

Foot pump 110 has a housing 120 which consists of two major parts, a housing base 111 and a housing cover or foot pedal 112. These two parts are joined at one end by a transverse shaft 113 which serves as a hinge for this pivotal engagement. Coiled springs 114 surround both ends of shaft 113 and cause foot pedal 112 to raise away from base 111 to the open position illustrated in FIG. 8. At the opposite end of base 111 there is a rotating leaf or end wall 115 which is hinged upon a second transverse shaft 116. Base end wall 115 is connected to a threaded sleeve or holder 122 which has a female or male fitting 118 for attaching tubular line 150 in an air-tight manner. Located near the middle of foot pedal 112 there is a third transverse shaft 116 which is also fitted with a rotating leaf or end wall 124 (not shown in FIG. 8) that functions as a clamp or grip.

Figure 9:
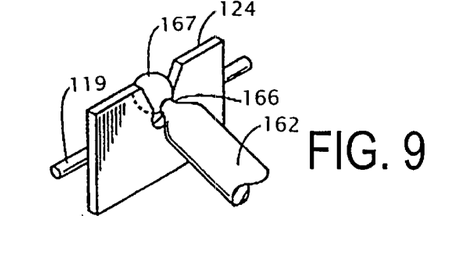
FIG. 9 is an enlarged portion of FIG. 8 showing a clamp arrangement for attachment of a reciprocating pump within a foot pump housing.

The purpose of the end wall attachments described above is to provide a means for a syringe-type unit or reciprocating pump 160 to be attached to base 111 and foot pedal 112 in a detachable manner. A threaded cylinder end 174 (not shown in FIG. 8) on piston cylinder 164 is connected to threaded holder 122 on base 111, and a piston rod or plunger 162 is attached to end wall clamp 124, which is depicted in FIG. 9. Reciprocating pump 160 may be easily detached from housing 120 for periodic cleaning and/or for conversion to a smaller hand operated breast pump that will be described later.

FIG. 9 shows plunger 162 of reciprocating pump 160 attached to end wall clamp 124 which pivots inside foot pedal 112 via transverse shaft 119. End wall clamp 124 preferably comprises a grip constructed of a deformable material, such as silicon, with an opening smaller than plunger neck 166 but large enough to accommodate this piece under moderate pressure. Plunger 162 is thereby pivotally attached to foot pedal 112 and moves in and out of piston cylinder 164, which is pivotally attached to base 111, by a pedal motion 170 shown in FIG. 8.

Figure 10:
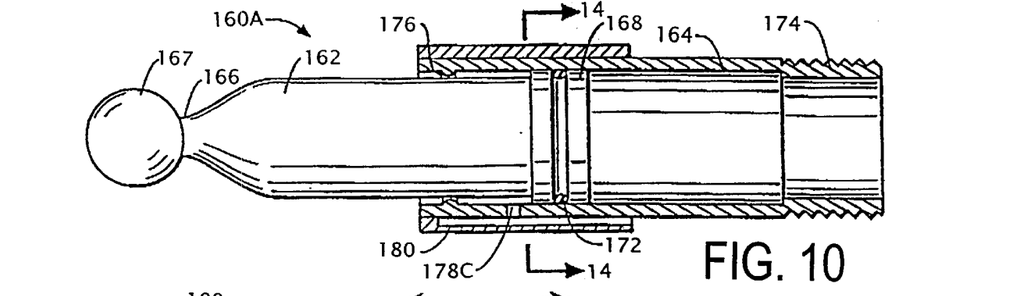
FIG. 10 is a side elevational view in partial section of a reciprocating pump detached from a foot pump housing.

In FIG. 10, an enlarged cross-sectional view of an alternate reciprocating pump 160A is shown detached from foot pump housing 120, along with the in and out or reciprocating motion 171 of the pump. A plunger head 168 is constructed of a rubber material or, alternatively, there is at least one O-ring 172 that provides an air-tight seal with the interior of the piston cylinder 164 so that a negative pressure or partial vacuum is developed when plunger 162 is pulled outward from piston cylinder 164. There is a lip or bead 176 on the interior of piston cylinder 164 that prevents plunger 162 from being pulled completely out of piston cylinder 164 and holds the device in the open position shown in FIG. 8 against the force of coiled springs 114.

The volume of piston cylinder 164 is such that on the vacuum producing stroke sufficient negative pressure is generated in receiving members 131 to cause milk to be expressed from both breasts simultaneously. The negative pressure required is presently considered to range from 100 to 250 mm Hg. In order to closely simulate the suck and release action of a nursing infant, there is also preferably provided at least one small aperture or hole 178 in the wall of the piston. This causes the maximum vacuum produced on the outward, vacuum producing stroke to be suddenly released when O-ring 172 passes this hole near the end of the stroke.

Figure 11:
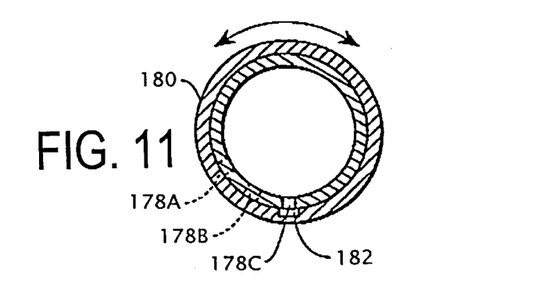
FIG. 11 is an enlarged cross-sectional view of the reciprocating pump taken along line 11—11 in FIG. 10 which shows an optional means for adjusting the maximum vacuum generated by a reciprocating pump.

The embodiment of reciprocating pump 160 depicted in FIG. 10, i.e. alternate reciprocating pump 160A, also includes an optional means for adjusting the maximum vacuum produced. This consists of two or more holes 178 in the rear wall of piston cylinder 164 that are located at varying distances from inner bead 176 and are spaced at equal intervals about the circumference of piston cylinder 164. A ring or cylinder collar 180 is provided adjacent to the rear end of piston cylinder 164 which covers all of the holes 178 in the piston wall. This arrangement is also shown in FIG. 11, which is a crosssection of alternate reciprocating pump 160A taken along line 11—11 in FIG. 10, and in FIG. 12 which includes an exploded view of the same. Cylinder collar 180 may be rotated and preferably is made of a semi-flexible material which enables a good seal between collar 180 and the exterior wall of piston cylinder 164. A longitudinal interior channel or passage 182 on cylinder collar 180 provides access to the atmosphere for only one of the holes 178 at a time. The operator may rotate cylinder collar 180 to select any of the holes 178 provided by aligning interior passage 182 with one of the position marks 184, shown in FIG. 12, on the exterior of piston cylinder 164. It will be appreciated that the effective working volume of piston cylinder 164 will change according to which hole 178 is selected, thereby changing the maximum negative pressure that is generated by the outward stroke. Preferably, position marks 184 should be labeled to clearly indicate which positions are the maximum and minimum (this is not shown for clarity). This optional means for adjusting the maximum vacuum produced enables the operator to adjust the suction applied to her nipples; which will vary according to the fit of receiving members 131 on her breasts, the amount of suction required for milk expression, and her own personal comfort level. Equally important, it also enables alternate reciprocating pump 160A to be more readily adaptable to an optional compact hand operated breast pump.

Figure 12:
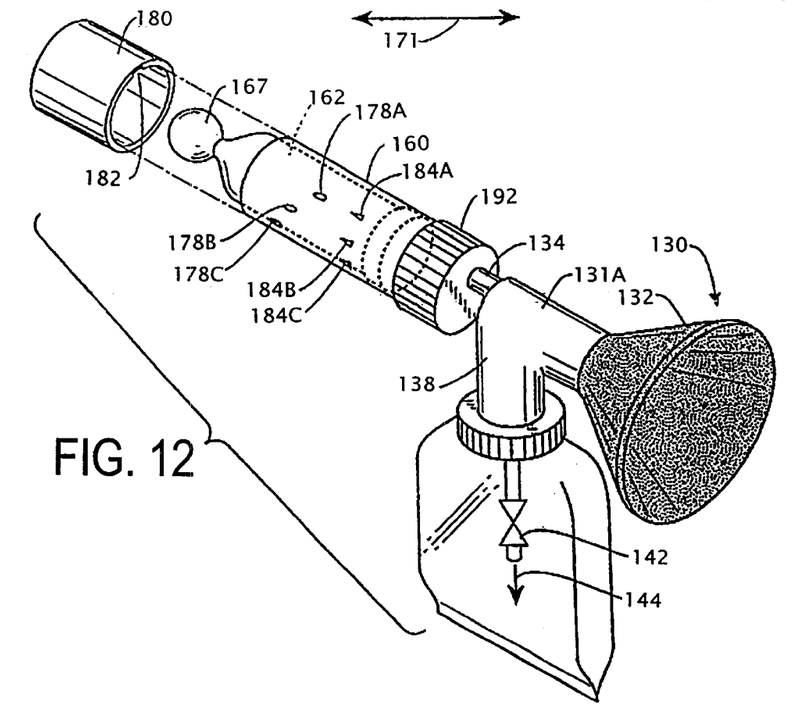
FIG. 12 is an exploded perspective view of a reciprocating pump assembled with a collection assembly for optional hand operation.

FIG. 12 depicts an embodiment of the present invention assembled for hand operation. It will be understood that since it takes two hands to pump a single breast with this device, this is not the preferred embodiment of the present invention. However, it will be appreciated that since this embodiment is even more compact than the entire foot operated assembly, it provides an added degree of flexibility. It will also be appreciated that no additional parts are required for this option, a single modification to one of the receiving members 131, depicted in FIG. 8 as an alternate receiving member 131A, is all that is necessary. A threaded sleeve or holder 192 (similar to holder 122 attached to base end wall 115) has been added to upper opening 134 of alternate receiving member 131A. Reciprocating pump 160 (or 160A) has been attached to holder 192, via threaded cylinder end 174, to complete the assembly. It will be understood that there is still provided a male or female fitting (not shown) inside or adjacent to holder 192 for attaching tubular line 150 to upper opening 134 in an air-tight manner for the preferred operation with the foot operated vacuum pump 110.

Figure 13:
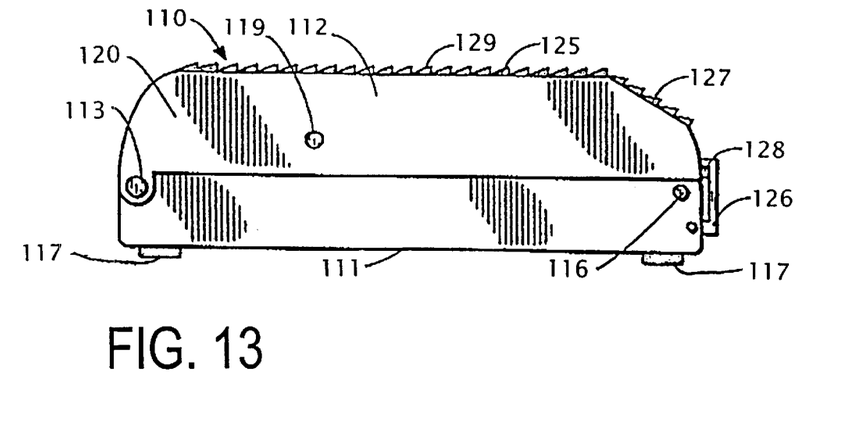
FIG. 13 is a side elevational view of a foot actuated breast pump in the closed or storage position.

For storage and transportation of the present invention foot operated vacuum pump 110 is converted to the more compact closed position, as depicted in FIG. 13. Note that tubular line 150 has been disconnected from fitting 118. Line 150 may be stored separately, or alternatively, it may also be disconnected from collecting assemblies 130 and stored inside foot pedal 112 prior to closing the device. To store the device, foot pedal 112 is pushed down completely until it meets base 111 and then a bail or latch 126 is simply engaged with a latch fitting 128 on foot pedal 112 to hold the device in the closed position. Preferably, foot pedal 112, base 111, and latch 126 form a completely enclosed housing for reciprocating pump 160 in the closed position and protect it from damage or contamination. However, housing 120 should not be air-tight to prevent mildew from occurring during storage.

Note that base 111 is preferably fitted with rubber feet 117 to provide traction with the surface it is placed upon during operation. Similarly, the upper surface of foot pedal 112 preferably has a slightly rough or ridged surface 129 to provide traction for the soles of the operator's shoes or feet. Foot pedal 112 also preferably has at least two distinct surfaces, a main surface 125 and a secondary surface 127 which enable the device to be actuated in a variety of orientations, as described in the following section and schematically depicted in FIG. 14.

Each collection assembly 130, depicted in FIG. 8, is pressed by hand against the woman's breasts to form an air-tight seal around each nipple. It will be appreciated that the natural moisture present during this operation will enhance the seal formed between receiving members 131 and the breasts. A periodic negative pressure is then generated by pedal motion 170 which actuates reciprocating pump 160 and is transmitted to receiving members 131 via tubular line 150. This periodic negative pressure causes milk to be expressed from the mother's breasts which is collected in collection chambers 140.

Pedal motion 170 is preferably provided by the operator's foot via the foot actuated vacuum pump 110 depicted in FIG. 8. Foot pedal 112 is depressed downward by the operator's foot and coiled springs 114 provide the upward return motion. Coiled springs 114 provide sufficient force to create the vacuum required. It will be appreciated that the operator may adjust the rate that the vacuum is applied by controlling how fast she allows foot pedal 112 to return to the open position.

Figure 14:
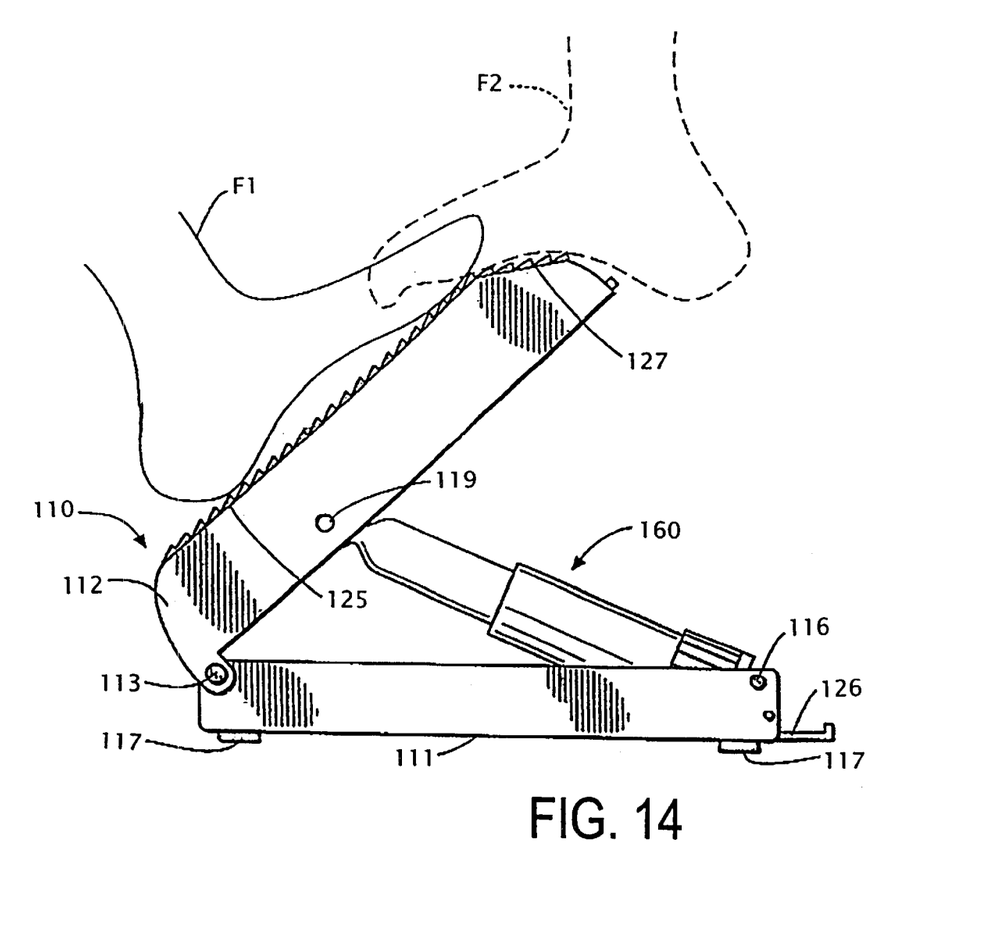
FIG. 14 is a schematic diagram showing alternate means of actuating the breast pump.

As illustrated by FIG. 14, foot pedal 112 may be actuated in at least two distinct orientations relative to the operator. Foot pedal 112 is designed such that the operator may push down on either main surface 125 using plantar flexion of the foot, or on secondary surface 127 utilizing the larger muscles of the upper leg. Additionally, it will be appreciated that the operator may also alternate feet during the pumping process. Accordingly, the device may be operated in a variety of orientations; this flexibility prevents tiring of the legs and repetitive motion stress by alternating which muscles are utilized.

Reciprocating pump 160, shown in FIG. 8, may be easily removed from housing 120 for periodic cleaning and/or for conversion to an optional hand operated breast pump, as shown in FIG. 12. To remove reciprocating pump 160, plunger 162 is first released from end wall clamp 124 and then piston cylinder 164 is unscrewed from internally threaded end wall holder 122. End wall clamp 124 may alternatively be a pivoting gallows device instead of the grip depicted in FIG. 9, or any other type of clamp which allows plunger 162 to be attached in a reversible manner. It will be appreciated that reciprocating pump 160 may be further disassembled, for cleaning purposes, by simply pushing plunger 162 out of the threaded end 174 of piston cylinder 164.

The optional hand operated breast pump embodiment depicted in FIG. 12 is simply actuated by pushing back and forth on plunger 162 with one hand, while pressing funnel-shaped receptacle 132 of receiving member 131A against the breast with the opposite hand. Accordingly, the end of plunger 162 should be designed so that it forms a grip 167 which can be comfortably grasped and pushed upon.

The manner of using the optional means for adjusting the maximum negative pressure depicted in FIGS. 10 through 12 and the steps for converting foot actuated vacuum pump 110 to the compact position shown in FIG. 13, have already been described in the previous section and will not be repeated here.

In light of the current teaching it is clear that the present invention provides a compact, lightweight, and economical device for the manual expression of breast milk from both breasts simultaneously. The device is simple to operate and not as physically demanding as the conventional hand operated breast pumps. It can be easily disassembled for cleaning and may also be converted to a compact hand operated device.

While the above description contains many specificities, these should not be construed as limitations on the scope of the invention, but rather as an exemplification of one preferred embodiment thereof. Many other variations are possible. For example, the foot actuated pump could be utilized to pump only one breast at a time. A wide variety of foot pump housing designs could be conceived to optimize the body mechanics involved in the pumping process. The foot pump could contain two reciprocating pumps, one for each breast, within the single housing. The housing could be actuated to the open position by a variety of mechanisms, such as a spring located within the piston cylinder of the reciprocating pump vice the pair of coiled springs shown here. The various parts of the apparatus may be constructed of any suitable material, which is determined primarily by factors such as cost, durability, and weight. Those having skill in the art may recognize additional modifications of elements which may facilitate the application of the invention, but still fall within the scope of the invention. Accordingly, the scope of the invention should be determined not by the embodiments illustrated, but by the appended claims and their legal equivalents.

What is claimed is:

1. A breast pump assembly, comprising:

a breast hood assembly including a breast-shield;

an otherwise manually operable piston pump having a piston cylinder with a chamber formed therein;

a hand-drivable piston received for reciprocating movement within said chamber to generate, in use, a periodic suction within said breast hood assembly for the expression of mother's milk, said piston cylinder having a forward end and a rearward end, the forward end having means for connecting said forward end directly to said breast-hood assembly including said breast-shield, said piston pump when operated in a first mode is directly connected to said breast-hood assembly generating said periodic suction in said breast-hood through movement of said piston in said piston cylinder, said piston having a piston rod connected thereto which has means thereon for grasping said piston rod to drive said piston, which piston rod extends out of said rearward end of said piston cylinder;

a base having a first mount releasably holding one of said piston cylinder forward end and said piston rod when said foot driven breast pump assembly is operated in a second mode; and a foot pedal hingeably attached to said base having a second mount releasably holding the other of said piston cylinder forward end and said piston rod when said foot driven breast pump assembly is operated in said second mode, said foot pedal being pivotable relative to said base to reciprocate said piston within said piston cylinder to generate said periodic suction with said piston pump received on said pedal and said base via said first and second mounts when operated by foot in said second mode of operation.

2. The breast pump assembly of claim 1 wherein said first mount comprises a slot formed into said base, said slot sized and shaped to receive said piston rod therein, and said second mount comprises a post in one of said piston cylinder and said pedal and a post hole on the other of said piston cylinder pedal, said post being received in said post hole to releasably hold said piston cylinder to said pedal.

3. A breast pump assembly, comprising:

a breast hood assembly including a breast-shield;

an otherwise manually operable piston pump having a piston cylinder with a chamber formed therein;

a hand-drivable piston received for reciprocating movement within said chamber to generate, in use, a periodic suction within said breast hood assembly for the expression of mother's milk, said piston cylinder having a forward end and a rearward end, the forward end having means for connecting said forward end directly to said breast-hood assembly including said breast-shield, said piston pump when operated in a first mode is directly connected to said breast-hood assembly generating said periodic suction in said breast-hood through movement of said piston in said piston cylinder, said piston having a piston rod connected thereto which has means thereon for grasping said piston rod to drive said piston, which piston rod extends out of said rearward end of said piston cylinder;

a base having a first means for releasably receiving and holding part of said piston pump;

a riser rigidly mounted on said base and forming a pivot;

a foot pedal having a second means for releasably receiving and holding another part of said piston pump;

a pivot mounting for said foot pedal on said riser so that one end of said pedal can alternatively pivot toward and then away from said base;

said first and second means for releasably receiving and holding said piston pump placing said piston pump in a configuration where pivoting movement of said pedal causes said piston to reciprocate within said cylinder to thereby generate a periodic suction when operated by foot in a second mode of operation.

4. A breast pump comprising:

a pedal drive having a pedal member, a base upon which said pedal is mounted, a pedal mount on said base to which said pedal member is attached for movement relative to said base;

a piston pump including a piston cylinder, a piston rod including a piston attached thereto, said piston reciprocally received within said piston cylinder for generating a periodic negative pressure within said piston cylinder, means for releasably affixing said piston cylinder directly to a breast shield assembly for conveying said periodic negative pressure to a breast placed within said shield for extraction of mother's milk when said piston pump is manually driven in a first mode of operation, said piston rod being adapted to be grasped; and means on said pedal drive for releasably mounting said piston pump on said pedal drive such that said piston pump is foot driven in a second mode of operation.

5. A breast pump, comprising:

a breast shield assembly including a breast shield adapted to overlie and receive a breast therein, and a container in fluid connection with said breast shield to receive milk extracted from the breast;

a piston pump having a piston cylinder which is releasably connected through a mating screw engagement directly to said breast shield assembly and which is manually drivable in a first mode of operation to generate a periodic negative pressure within said breast shield to pull and massage a breast placed within said shield to extract milk;

a pedal drive having a pedal member, a base upon which said pedal is mounted, and a pedal mount to which said pedal member is attached for movement relative to said base; and a mounting mechanism on said pedal drive for releasably mounting said pump to said pedal drive to render said pump drivable by said pedal member in a second mode of operation.

6. The breast pump of claim 5 wherein said pump is a piston pump including a piston rod for reciprocally driving a piston fixed on said rod which is received within a piston cylinder, said piston rod being adapted to be grasped for manually driving said piston pump in said first mode of operation, one of said piston rod and piston cylinder being mounted to said pedal member by said mounting mechanism and the other of said piston rod and piston cylinder being mounted to said base by said mounting mechanism, whereby movement of said pedal member drives said piston pump in said second mode of operation.

7. The breast pump of claim 6 further including an adapter for said piston pump forming part of said mounting mechanism, said adapter being received on an end of said piston cylinder opposite from an end through which said piston rod extends, said adapter having an interior channel in communication with a piston cylinder interior and an outlet to said channel to which outlet tubing is connected to covey periodic negative pressure generated in said piston cylinder interior to said breast shield, said adapter further including a member received on one of said pedal member and said base to releasably attach said piston cylinder thereto.

8. The breast pump of claim 7 wherein said adapter member is a post which is received within a bore formed in one of said pedal member and said base, and said piston rod is received in a slot formed in the other of said pedal member and said base, said slot being part of said mounting mechanism.

9. The breast pump of claim 8 wherein a plurality of bores are formed along a side of one of said pedal member and said base to selectively receive said adapter member therein to adjust the stroke of said piston rod relative to maximum movement of said pedal member.

10. The breast pump of claim 7 wherein said piston pump further includes a spring within said piston cylinder which spring bears against said piston and said adapter to bias an end of said pedal member away from said base with said piston pump attached to said pedal drive.

11. The breast pump of claim 7 wherein said adapter is mountable on an electrically driven motor drive mechanism to drive said piston pump in a third mode of operation, said piston pump being readily and releasably attachable to each of said breast shield assembly, said pedal drive and said motor drive to switch between each of said three modes of operation.

12. The breast pump of claim 5 wherein said pedal mount is releasably attached to said base.

* * * * *